US008234907B2

(12) United States Patent
Helwegen et al.

(10) Patent No.: US 8,234,907 B2
(45) Date of Patent: Aug. 7, 2012

(54) PHOTO ACOUSTIC DETECTOR WITH IMPROVED SIGNAL PROCESSING

(75) Inventors: Ivon Franciscus Helwegen, Herten (NL); Hans Willem Van Kesteren, Eindhoven (NL)

(73) Assignee: Koninklijke Philips Eletronics N.V., Eindhoven (NL)

( * ) Notice: Subject to any disclaimer, the term of this patent is extended or adjusted under 35 U.S.C. 154(b) by 363 days.

(21) Appl. No.: 12/513,523

(22) PCT Filed: Nov. 2, 2007

(86) PCT No.: PCT/IB2007/054444

§ 371 (c)(1), (2), (4) Date: May 5, 2009

(87) PCT Pub. No.: WO2008/056307

PCT Pub. Date: May 15, 2008

(65) Prior Publication Data

US 2010/0043526 A1 Feb. 25, 2010

(30) Foreign Application Priority Data

Nov. 10, 2006 (EP) .................................... 06123851

(51) Int. Cl.
*G01N 21/00* (2006.01)

(52) U.S. Cl. ...................................................... 73/24.02

(58) Field of Classification Search ................. 73/24.02, 73/24.06; 356/432, 436, 437, 441, 442
See application file for complete search history.

(56) References Cited

U.S. PATENT DOCUMENTS

| | | | |
|---|---|---|---|
| 4,303,343 A | 12/1981 | Patel et al. | |
| 4,722,602 A | 2/1988 | Kitamori et al. | |
| 4,808,828 A | 2/1989 | Kitamori et al. | |
| 6,160,255 A | 12/2000 | Sausa | |
| 6,606,121 B1 | 8/2003 | Bohm et al. | |
| 2005/0117155 A1 | 6/2005 | Kosterev | |

FOREIGN PATENT DOCUMENTS

| | | |
|---|---|---|
| JP | 59231426 A | 12/1984 |
| WO | 03104767 A2 | 12/2003 |
| WO | 2008056312 A1 | 5/2008 |

OTHER PUBLICATIONS

Optical Society of America—Bass, Michael, Editor (1995). Handbook of Optics, vol. I—Fundamentals, Techniques and Design (2nd Edition). (pp. 18.13-18.16). McGraw-Hill.*

Kosterev et al: "Applications of Quartz Tuning Forks in Spectroscopic Gas Sensing"; Review of Scientific Instrunemtns, vol. 76, No. 4, Mar. 2005, pp. 043105-1-043105-9.

* cited by examiner

*Primary Examiner* — Hezron E Williams
*Assistant Examiner* — Jamar Ray

(57) ABSTRACT

A photo acoustic detector for detecting a concentration of a sample in a mixture includes a light source for producing a light beam for exciting molecules of the sample, and a light modulator for modulating the light beam for generating pressure variations in the sample mixture, where an amplitude of the pressure variations is a measure of the concentration. The detector further includes a detector element for converting the pressure variations into a detector current and a processing section for processing the detector current to generate an output signal representing the concentration. The processing section includes an integrating amplifier for integrating the detector current, the integrating amplifier being coupled to the detector element via a hold switch, and a timing circuit for generating a hold signal, $SW_{HOLD}$, for operating the hold switch to couple the integrating amplifier to the detector element during a predetermined interval of the detector current.

11 Claims, 5 Drawing Sheets

PHOTO ACOUSTIC DETECTOR WITH IMPROVED SIGNAL PROCESSING

CROSS REFERENCE TO RELATED APPLICATION

This application claims the benefit of EP provisional application s/n 06123851.5, filed Nov. 10, 2006, which is incorporated herein by reference. A related application is PCT IB2007/054472, "Oscillator Element for Photo Acoustic Detector," filed Nov. 5, 2007, published as WO 2008/056312.

TECHNICAL FIELD OF THE INVENTION

The invention relates to a photo acoustic detector for detecting a concentration of a sample in a sample mixture, the photo acoustic detector comprising a light source for producing a light beam for exciting molecules of the sample, a light modulator for modulating the light beam for generating pressure variations in the sample mixture, an amplitude of the pressure variations being a measure of the concentration, a detector element for converting the pressure variations into a detector current, and a processing section for processing the detector current to generate an output signal representing the concentration.

BACKGROUND OF THE INVENTION

Such a photo acoustic detector is known from the United States patent application, published as US 2005/0117155. Said patent application describes a photo acoustic trace gas detector using a quartz tuning fork for detecting the pressure variations. Light modulation is performed using amplitude or wavelength modulation. After amplification by a pre-amplifier, a lock-in amplifier mixes the detector signal with a reference signal for acquiring an output signal. The reference signal for the lock-in amplifier is taken from a signal for modulating the light beam. The use of the quartz tuning fork for the detection of the pressure variations allows for a relatively compact photo acoustic trace gas detector.

An application of photo acoustic trace gas detectors is breath testing. Breath testing is a promising area of medical technology. Breath tests are non-invasive, user friendly and low cost. Prime examples of breath testing are monitoring of asthma, alcohol breath testing and detection of stomach disorders and acute organ rejection. First clinical trials show possible applications in the pre-screening of breast and lung cancer. These volatile biomarkers have typical concentrations in the parts per billion (ppb) range. Nitric oxide (NO) is a well known trace gas in the human breath, and elevated concentrations of NO can be found in asthmatic patients. Currently, exhaled NO levels at ppb concentrations can only be measured using expensive and bulky equipment based on chemiluminescence or optical absorption spectroscopy. A compact, low-cost NO sensor forms an interesting device that can be used to diagnose and monitor airway inflammation and can be used at the doctor's office and for medication control at home.

It is a problem of the photo acoustic trace gas detector according to US 2005/0117155 that the detector currents during trace gas detection are often very low and easily dominated by electronic noise, which limits the trace gas detection at low concentrations.

SUMMARY OF THE INVENTION

It is an object of the invention to provide a photo acoustic detector according to the opening paragraph, which detector has a lower detection limit than state of the art detectors.

According to a first aspect of the invention, this object is achieved because the processing section comprises an integrating amplifier for integrating the detector current, the integrating amplifier being coupled to the detector element via a hold switch, and a timing circuit for generating a hold signal, $SW_{HOLD}$, for operating the hold switch in order to couple the integrating amplifier to the detector element during a predetermined interval of a period of the detector current.

The detector element provides a detector current that oscillates at the resonance frequency of the pressure variations induced by the light source in the sample mixture. The operating of the hold switch in the integrating amplifier results in sampling only a predetermined interval during a period of the detector current. The fixed interval is chosen shorter than the whole period, because the positive part of the oscillating detector current compensates the negative part and, as a consequence, the integrated value of the detector current over a whole period does not depend on the amplitude of the pressure variations. Integrating the detector current over a whole period does not provide information about the concentration of the sample in the sample mixture. By only integrating a shorter predetermined interval of the signal, this compensation does not occur and a higher amplitude results in a higher integrated value. Each obtained signal sample is a measure of the concentration of the sample. By adding the obtained signal samples for multiple periods of the detector current, the gain of the output signal is improved and lower sample concentration can be detected.

Preferably, the timing circuit is arranged for operating the hold switch repeatedly by generating the hold signal, $SW_{HOLD}$, as a periodic signal with a frequency equal to the frequency of the detector current and a duty cycle of 50%.

Preferably the detector current and the hold signal, $SW_{HOLD}$, are in phase or in antiphase. By sampling 50% of each period of the detector current, only the positive part of the detector current or only the negative part of the detector current is integrated. By adding only the positive parts of multiple periods of the signal from the oscillator element, the gain and the signal to noise ratio of the detector is much improved, thereby resulting in a more sensitive photo acoustic detector. When the detector current and the hold signal $SW_{HOLD}$ are not exactly in phase or in antiphase, the gain of the detector decreases.

Preferably, the detector element is an oscillator element and the light modulator is arranged for modulating the light beam at a resonance frequency of the oscillator element.

Due to its small bandwidth, such an oscillator element is less sensitive to environmental acoustic noise. The detector current from such an oscillator is highly sinusoidal, which makes it very suitable for use with the processing schemes described below.

In another embodiment of the photo acoustic detector, the timing circuit is arranged for operating the hold switch repeatedly by generating the hold signal, $SW_{HOLD}$, as a periodic signal with a frequency equal to one third of the frequency of the detector current and a duty cycle of 50%.

In this embodiment the detector current is integrated once every three periods and the fixed interval during which the detector current is integrated comprises two positive and one negative part (or vice versa). One positive part compensates for the negative part and the second positive part contributes to the output signal. Also in this embodiment, the detector current and the hold signal, $SW_{HOLD}$, are preferably in phase or in antiphase.

This embodiment also eliminates disadvantages of the above described embodiment wherein the hold signal, $SW_{HOLD}$, has a frequency equal to the frequency of the detector current and a duty cycle of 50%. That embodiment, if combined with the use of an oscillator element for detection of the pressure variations, shows the disadvantage that the hold switch switches at the same frequency as the resonance frequency of the detector signal. When the hold switch (typically a FET) switches, some small current flows through this switch at the resonance frequency of the oscillator element. As a result the oscillator gets excited a bit, causing an offset in the output signal. So even without laser light and sample molecules, an offset at the output occurs. When switching the hold signal, $SW_{HOLD}$, at a frequency equal to one third of the frequency of the detector current the hold switch is not operated at the resonance frequency of the oscillator element and the oscillator element does not resonate anymore on switching $SW_{HOLD}$. As a result, the switching does not influence the detector current.

In another embodiment, a similar effect is achieved by generating the hold signal, $SW_{HOLD}$, as a periodic signal with a frequency equal to half of the frequency of the detector current and a duty cycle of 75%.

This embodiment has the additional advantage, that the time needed for taking a sample is shorter than in the previous embodiment. This results in faster detection with the same signal to noise ratio, or equally fast detection with a better signal to noise ratio. In another embodiment, the processing section is arranged for taking a first and a second measurement by respectively generating a first and a second output signal, the hold signal, $SW_{HOLD}$, used for the second measurement being phase shifted over half a period of the detector current, and calculating an average output signal from the absolute values of the first and the second output signal.

In this embodiment the offset caused by the switching of the hold switch is averaged out. The first measurement gives a positive result and the second measurement gives a negative result, but both carry the same offset.

In yet another embodiment, the hold switch is coupled to the oscillator element via a buffer stage. The buffer stage results in some extra gain. The buffer stage also results in offset canceling, because there is no direct coupling anymore between the detector element and the hold switch.

In a preferred embodiment, the processing section further comprises a select switch for copying an integrated voltage from the integrating amplifier to the output signal and a reset switch for resetting the integrating amplifier and wherein the timing circuit is arranged for generating a select signal, $SW_{SELECT}$, for operating the select switch and a reset signal, $SW_{RESET}$, for successively operating the reset switch and wherein the timing circuit is further arranged for generating the hold signal, $SW_{HOLD}$, with a frequency of at least twice a frequency of the reset signal, $SW_{RESET}$.

In this embodiment, the integrated detector currents of at least two, but preferably more, consecutive samples are summed. For a higher signal to noise ratio, more samples are collected before copying the capacitor charge to the output signal and resetting the capacitor for starting a new measurement.

In a preferred embodiment of the photo acoustic detector the processing section further comprises a post processing unit with a comparator for comparing an integrated voltage from the integrating amplifier to a predetermined value, a reset pulse generator for, when the integrated voltage reaches the predetermined value, providing a reset pulse, $SW_{RESET}$, for closing a reset switch and resetting the integrating amplifier, and a timer for, when the integrated voltage reaches the predetermined value, determining a total sampling time used for reaching the predetermined value.

For small detector currents, more gain is needed to obtain sufficient signal to noise ratio, which results in a longer integration time. For large detector currents however, less gain is needed, which results in a shorter integration time. By adaptively calculating the total sampling time, the signal to noise ratio can be kept sufficient and the integration time can be kept as short as possible.

These and other aspects of the invention are apparent from and will be elucidated with reference to the embodiments described hereinafter.

DETAILED DESCRIPTION OF THE INVENTION

Figure 1:
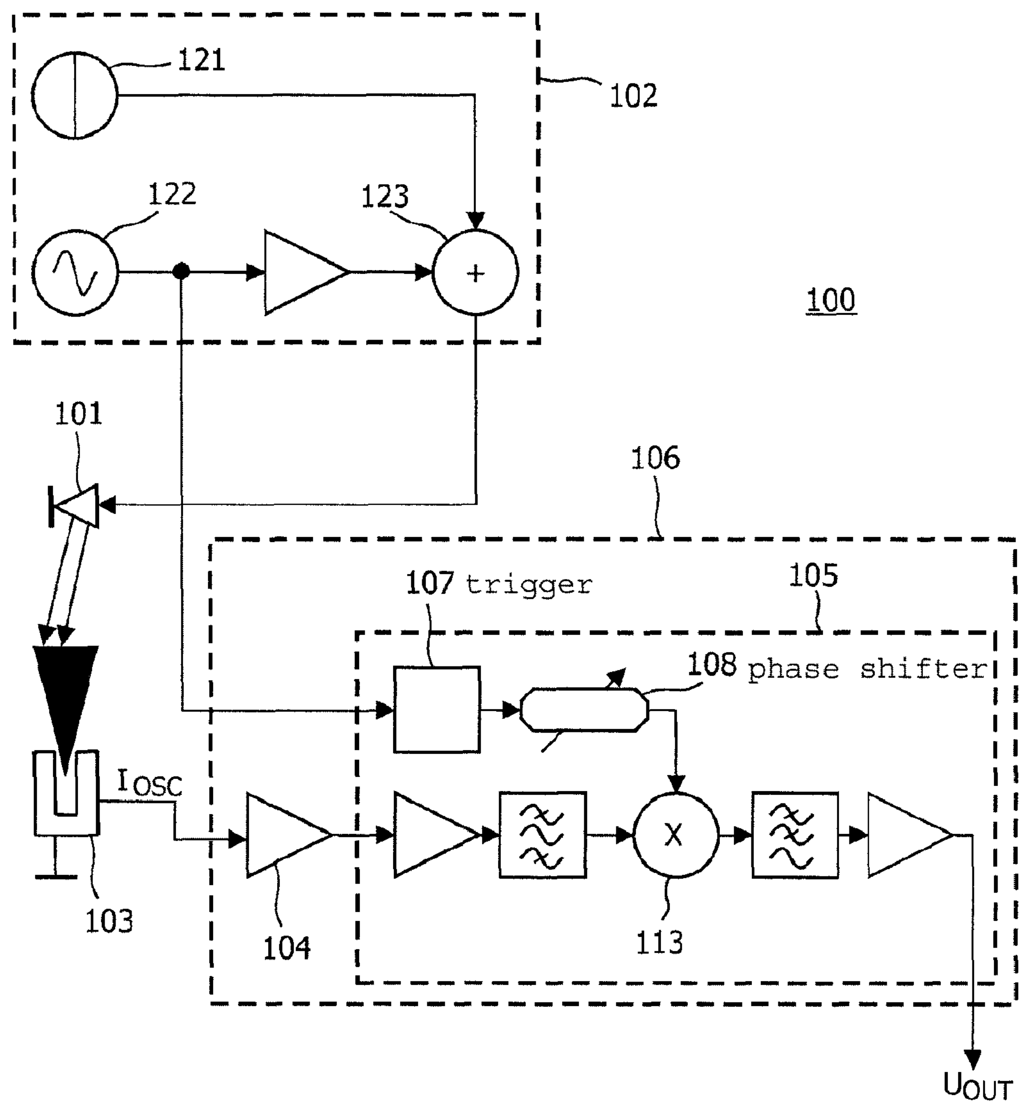
FIG. 1 schematically shows a prior art photo acoustic trace gas detector.

FIG. 1 schematically shows a prior art photo acoustic detector. The photo acoustic trace gas detector described hereinafter detects trace gas concentrations in gas mixture, but the invention may also be applied to detect tissue, fluid or solid samples in other sample mixtures. The trace gas detector 100 uses a laser diode 101 as a light source. The wavelength of the laser light is chosen such that it can excite the trace gas molecules. Alternatively, other types of laser sources or other light sources, capable of producing a light beam with sufficient energy to excite the trace gas molecules may be used. A laser driver 102 provides a driving signal for the laser diode 101. In this embodiment, the laser driver 102 also functions as a modulator for modulating the light beam. The laser driver 102 comprises a DC source 121 for providing a DC signal and an AC source 122 for providing an AC signal. The DC signal and the AC signal are combined in adder 123 and then provided to the laser diode 101. As a result, the intensity of the light beam changes in time, following a sinusoidal pattern. A higher intensity of the laser beam results in more molecules in the trace gas being excited, which leads to a higher temperature of the gas mixture. A larger amplitude of the driving signal results in larger temperature fluctuations. A higher concentration of the trace gas also results in larger temperature fluctuations. The temperature fluctuations cause pressure variations or sound waves in the gas mixture. The pressure variations are detected by a detector element, such as a microphone or an oscillator element 103. If the laser light is modulated at the resonance frequency of an oscillator element 103, the sound waves excite the oscillator 103. Preferably, the oscillator element 103 is a crystal oscillator, such as a quartz tuning fork. Quartz tuning forks have a high sensitivity and operate at a high frequency. Furthermore, quartz tuning forks are not very expensive because they are used on large scale, for example, for the manufacturing of digital watches.

Modulation of the intensity of the light beam may also be realized by manipulating a light beam with a continuous intensity. It is, for example, known to us a mechanical chopper for generating an intensity modulated light beam from a continuous wave light beam.

In an alternative embodiment, the intensity of the light beam is constant and the wavelength of the laser light is modulated. This embodiment takes advantage of the effect that only light in a specific range of wavelengths is suited for exciting the trace gas molecules. For wavelength modulation, the laser is modulated with the half of the resonance frequency of the oscillator 103. The oscillator 103 then starts to resonate at its resonance frequency (wavelength modulation doubles the frequency).

The oscillating crystal oscillator 103 generates a small oscillating detector current $I_{osc}$ with a frequency, equal to the resonance frequency of the oscillator 103 and with an amplitude, proportional to the trace gas concentration. A signal processing unit 106 processes the detector current $I_{OSC}$ to provide an output signal $U_{OUT}$, indicative of the trace gas concentration. The prior art processing unit comprises a pre-amplifier 104 and a lock-in detector 105. The pre-amplifier 104 amplifies this current $I_{OSC}$. Lock-in detection does the generation of the actual output. The lock-in detector 105 mixes the amplified signal with a reference signal that has the same phase as the amplified signal. The reference signal is derived from the AC laser signal. A trigger 107 and a phase shifter 108 are used for providing the reference signal to a mixer 113. The mixer 113 mixes the reference signal with the amplified signal. The mixer output is low pass filtered, so a DC output $U_{OUT}$ represents the detected trace gas concentration.

Figure 2:
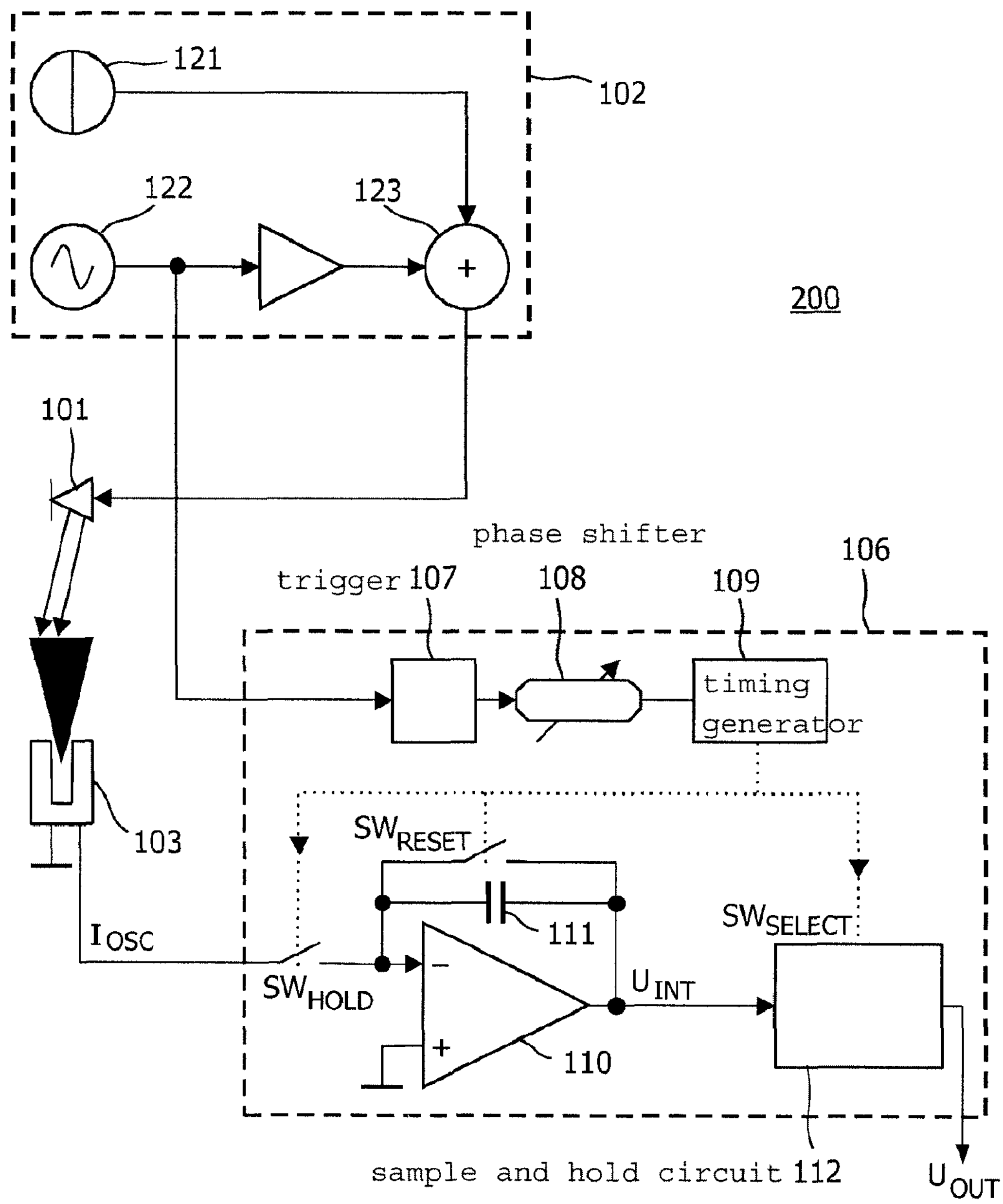
FIG. 2 schematically shows a photo acoustic trace gas detector according to the invention.
Figure 3:
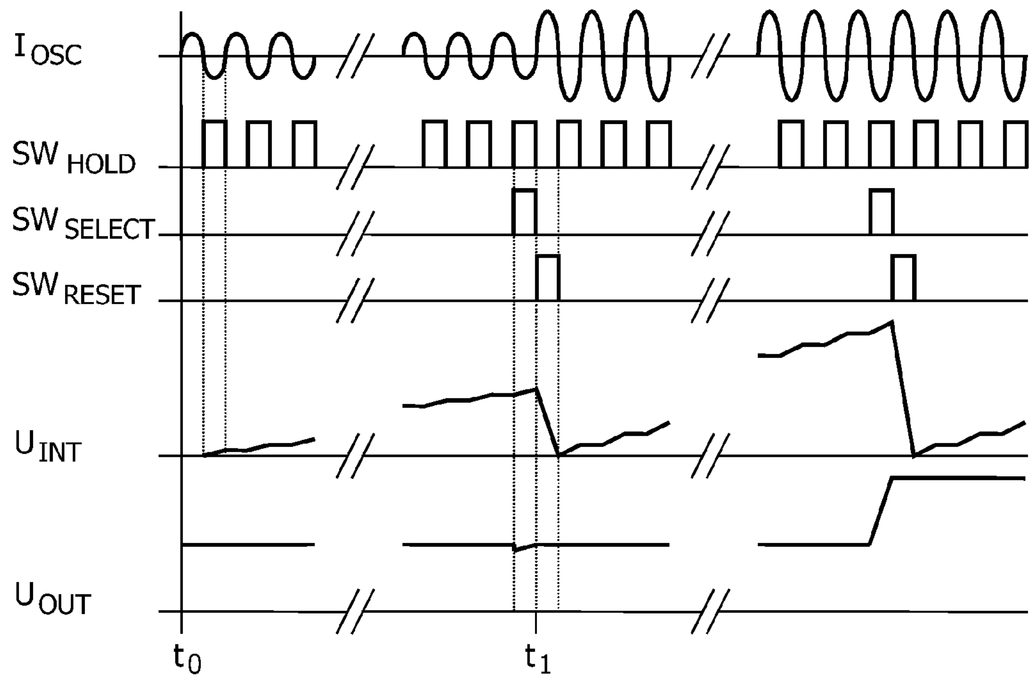
FIG. 3 shows a collection of signals demonstrating the operation of the photo acoustic trace gas detector according to FIG. 2.

FIG. 2 schematically shows a photo acoustic trace gas detector 200 according to the invention. According to the invention, the pre-amplifier 104 and the lock-in detector 105 are replaced by an integrating amplifier with a special switching algorithm to do the pre-amplification and the generation of the output signal $U_{OUT}$. The actual mixing is done in the integrator, so external lock-in detection is not needed anymore. The laser diode 101 is again supplied with an AC and DC current. The light induced pressure variations excite the oscillator 103 and the integrating amplifier amplifies the detector current $I_{OSC}$. The integrator shown in FIG. 2 comprises an op-amp 110 and a capacitor 111, interconnecting the output of the op-amp 110 with the negative input of the op-amp 110. The integrator has 3 switches to be controlled. A hold switch is used to store the oscillator current $I_{OSC}$ into a capacitor 111. This switch needs to be in phase with $I_{OSC}$. A reset switch resets the integrator when needed and a select switch copies the integrated output value $U_{INT}$ to the output. A trigger 107 together with a phase shift circuit 108 is used to get the switching signal $SW_{HOLD}$ for the hold switch, in phase with $I_{OSC}$. A timing generator block 109 (normally a small piece of digital logic) generates the switching signals from the AC laser frequency. Every once in a while (e.g. 10 or 100 times per second) the timing generator block 109 generates a select signal $SW_{SELECT}$ and the integrated signal $U_{INT}$ is copied to the output. Directly after that, a reset signal $SW_{RESET}$ resets the capacitor 111. So the gain also depends on the reset frequency. FIG. 3 shows a collection of signals demonstrating the operation of the photo acoustic trace gas detector 200 according to FIG. 2. In FIG. 3, the following signals are shown:

$I_{OSC}$: The signal from the oscillator 103. The frequency of the signal is the same as the frequency of the AC modulation frequency of the amplitude modulation or, when wavelength modulation is used, twice the AC modulation frequency of the wavelength modulation. The amplitude of $I_{OSC}$ is proportional to the concentration of the trace gas. FIG. 3 shows one increase of the trace gas concentration. At $t=t_1$ the trace gas concentration and the detector current $I_{OSC}$ roughly double.

$SW_{HOLD}$: The hold signal, $SW_{HOLD}$, controls the hold switch. When $SW_{HOLD}$ is high, the switch is closed. When $SW_{HOLD}$ is low, the switch is open. A comparison of $I_{OSC}$ and $SW_{HOLD}$ shows that only the negative parts of the detector current $I_{OSC}$ are fed to the capacitor 111. When $I_{OSC}$ is positive, the hold switch is open and $I_{OSC}$ is not integrated by the capacitor 111. In this example, the frequency of $SW_{HOLD}$ is the same as the frequency of $I_{OSC}$ and the duty cycle is 50%.

$U_{INT}$: When the hold switch is closed and the detector current $I_{OSC}$ is fed into the capacitor 111, the voltage, $U_{INT}$, at the output of the op-amp 110 increases. When the hold switch is open, $U_{INT}$ remains constant. $SW_{SELECT}$: Every once in a while (e.g. 10 or 100 times per second) the select signal, $SW_{SELECT}$, is high and the voltage $U_{INT}$ is sampled by a sample and hold circuit 112.

$SW_{RESET}$: Directly after sampling $U_{INT}$, a reset signal, $SW_{RESET}$, causes a reset switch to close and the integrator is reset. Thereafter, the integrator starts integrating the detector current $I_{OSC}$ again and continues to do so until the next reset. A high reset frequency results in a high sampling rate, but a relatively low gain. A low reset frequency results in a lower sampling rate and a higher gain. The gain thus also depends on the reset frequency.

$U_{OUT}$: The sample and hold circuit provides the output signal, $U_{OUT}$. As shown in FIG. 3, the trace gas concentration increases at $t=t_1$ (the amplitude of $I_{OSC}$ increases) and the output signal, $U_{OUT}$, changes the first time that a new sample is taken ($SW_{SELECT}$ is high).

Figure 4:
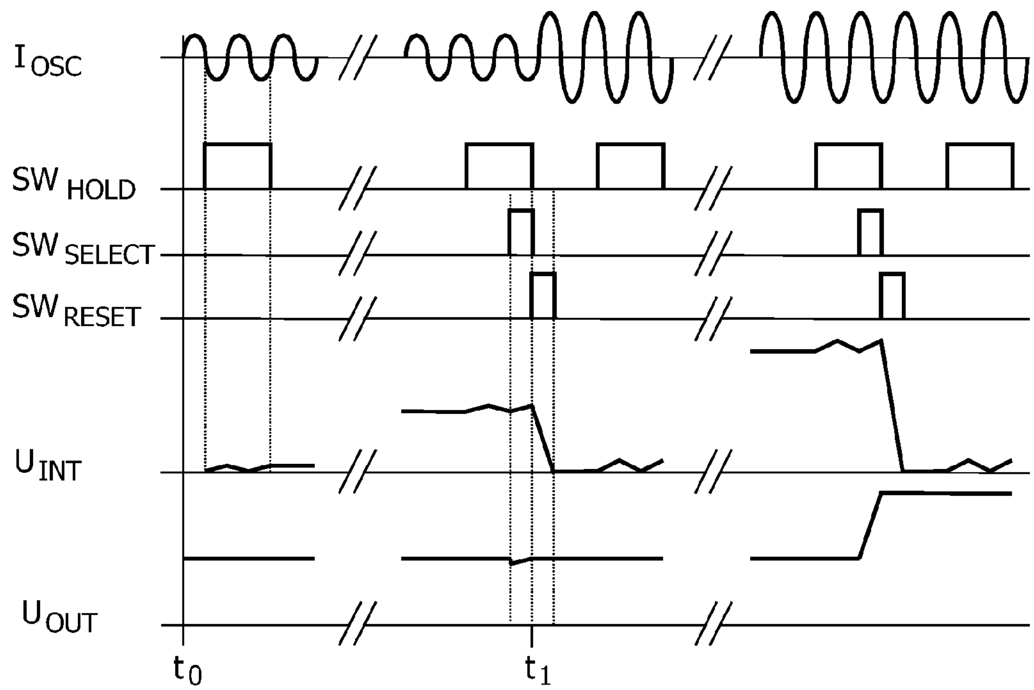
FIG. 4 shows a collection of signals demonstrating the operation of another embodiment of the photo acoustic trace gas detector according to FIG. 2, FIG. 5 schematically shows a preferred embodiment of the photo acoustic trace gas detector according to the invention.

The embodiment shown with reference to FIG. 3 has the disadvantage that the hold switch switches at the same frequency as the resonance frequency of the crystal oscillator. When the hold switch (typically a FET) switches, some small current flows through this switch at the resonance frequency of the crystal oscillator. As a result the oscillator gets excited a bit, causing an offset in $U_{OUT}$. So even without laser light and trace gas, an offset at the output occurs. This disadvantage does not occur in the embodiment which is demonstrated with reference to FIG. 4. FIG. 4 shows a collection of signals demonstrating the operation of another embodiment of the photo acoustic trace gas detector 200 according to FIG. 2. In this event, the frequency of $SW_{HOLD}$ is one third of the frequency of $I_{OSC}$ and the duty cycle is 50%. In this embodiment the detector current is integrated once every three periods and the fixed interval during which the detector current is integrated comprises two negative and one positive part. The first negative part compensates for the positive part and the second negative part contributes to the output signal $U_{OUT}$. Because the hold switch is not operated at the resonance frequency of the crystal oscillator, the switching does not influence the detector current $I_{OSC}$.

A similar effect is achieved by generating the hold signal, $SW_{HOLD}$, with a frequency equal to half of the frequency of the detector current $I_{OSC}$ and a duty cycle of 75%. This embodiment has the additional advantage, that the time needed for taking a sample is shorter than in the previous embodiment. This results in faster detection with the same signal to noise ratio, or equally fast detection with a better signal to noise ratio.

In principle all duty cycles of less than 100% for $SW_{HOLD}$ enable integrating the detector current $I_{OSC}$. However, a duty cycle of, for example, 1% or 99% would result in an improved gain only if the integration time is very long. Also for the frequency of $SW_{HOLD}$, a lot of different values may be selected. In all embodiments, it is important that a suitable combination of the frequency and duty cycle of $SW_{HOLD}$ and the frequency of $SW_{SELECT}$ and $SW_{RESET}$ is selected. Some examples of suitable combinations are described above. Alternatively, the frequency of $SW_{HOLD}$ may, e.g., be 99% of the frequency of the light modulation, which results in a low frequency mix signal. This low frequency mix signal may also be used as a measure for the sample concentration, if it is sampled at a suitable frequency.

In another embodiment, the processing section is arranged for generating a first and a second output signal, the hold signal, $SW_{HOLD}$, used for obtaining the second output signal being 180° phase shifted with respect to the detector current, and calculating an average output signal from the absolute values of the first and the second output signal. In this embodiment the offset caused by the switching of the hold switch and the resulting excitation of the crystal oscillator is averaged out. The first measurement gives a positive result and the second measurement gives a negative result, but both carry the same offset.

In yet another embodiment, the hold switch is coupled to the crystal oscillator via a buffer stage. The buffer stage results in some extra gain and prevents excitation of the detector by current from the hold switch. The gain of the buffer stage is kept sufficiently small so the noise current of the buffer stage stays far below the detector noise current.

Figure 5:
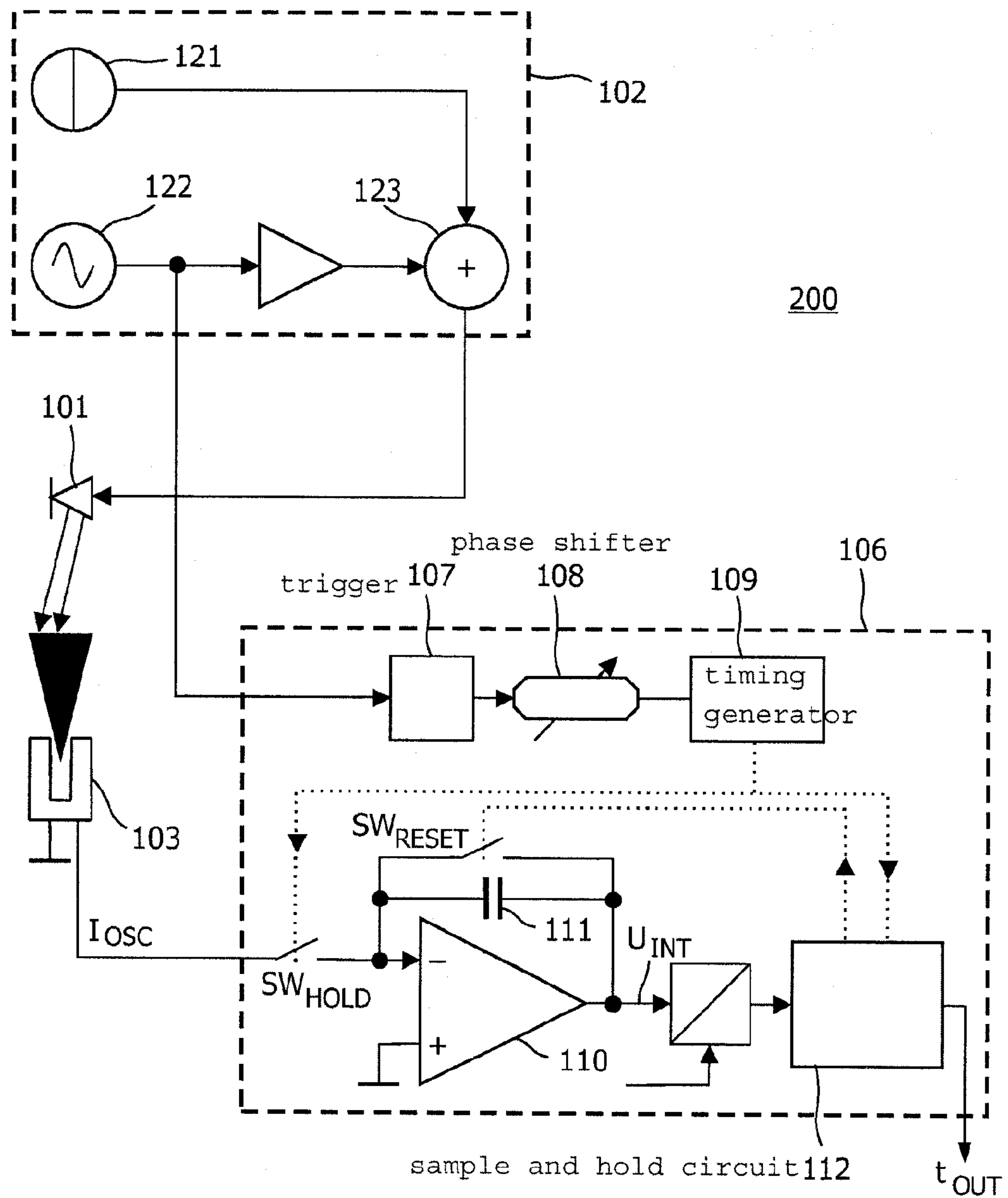

FIG. 5 schematically shows a preferred embodiment of the photo acoustic trace gas detector 200 according to the invention. In this embodiment the processing section 106 comprises a post processing unit 112 for comparing the integrated voltage $U_{INT}$ from the capacitor 111, to a predetermined value, determining a total sampling time used for reaching the predetermined value when the integrated voltage reaches the predetermined value and outputting the total sampling time as the output signal. For small detector currents, more gain is needed to obtain sufficient signal to noise ratio, which requires a longer integration time. For large detector currents however, less gain is needed, requiring a shorter integration time. By adaptively calculating the total sampling time, the signal to noise ratio can be kept sufficient and the integration time can be kept as short as possible.

Figure 6A:
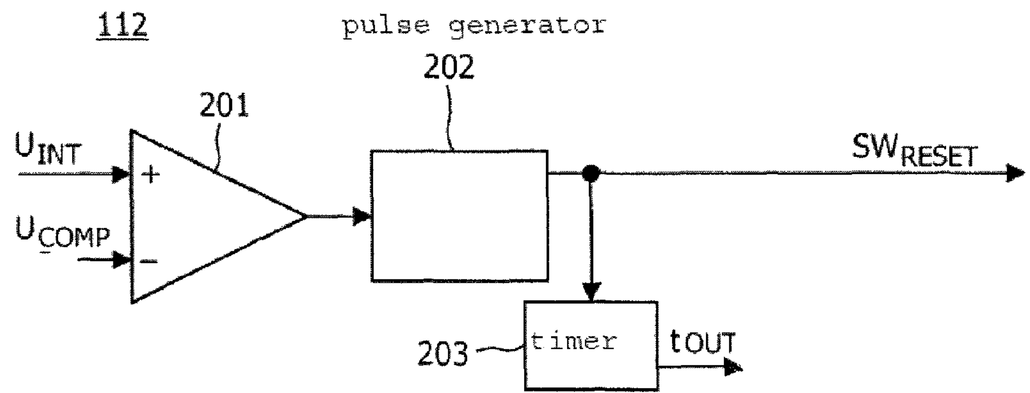
FIG. 6*a* shows an exemplary arrangement of the post processing unit comprised in the embodiment of FIG. 5.

FIG. 6*a* shows an exemplary arrangement of the post processing unit 112 comprised in the embodiment of FIG. 5. The post processing unit 112 comprises a comparator 201 for comparing the integrated voltage $U_{INT}$ from the capacitor 111, to the predetermined value, $U_{COMP}$. When the integrated voltage, $U_{INT}$, reaches the predetermined value, $U_{COMP}$, a reset pulse generator 202 provides a pulse, $SW_{RESET}$, for closing a reset switch and discharging the capacitor 111. The output $SW_{RESET}$ of the reset pulse generator 202 is also provided to a timer 203 for, when the integrated voltage reaches the predetermined value, determining a total sampling time used for reaching the predetermined value. When the trace gas concentration is higher, the predetermined value, $U_{COMP}$, is reached sooner and the time between two reset pulses will be shorter. The 'time to reset' thus is indicative of the trace gas concentration.

Figure 6B:
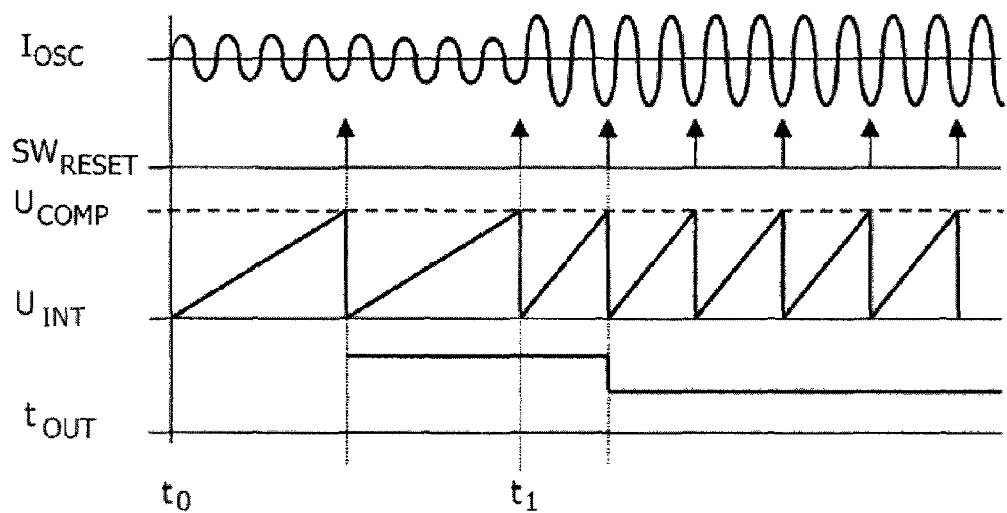
FIG. 6*b* shows a collection of signals demonstrating the operation of the embodiment shown in FIG. 5.

FIG. 6*b* shows a collection of signals demonstrating the operation of the embodiment shown in FIG. 5. Reset pulses, $RW_{RESET}$, are provided when $U_{INT}$, reaches $U_{COMP}$. After an increase of the amplitude of the oscillator current, $I_{OSC}$, the sampling time value, $t_{OUT}$, changes as soon as $U_{INT}$ reaches the predetermined value, $U_{COMP}$, for the first time. Smaller values for the sampling time value, $t_{OUT}$, relate to higher trace gas concentrations. For small detector currents, more gain is needed to obtain sufficient signal to noise ratio, which results in a longer integration time. For large detector currents however, less gain is needed, which results in a shorter integration time. By adaptively calculating the total sampling time, the signal to noise ratio can be kept sufficient and the integration time can be kept as short as possible.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the claims enumerating several means, several of these means may be embodied by one and the same item of hardware. The mere fact that certain measures are recited in mutually different dependent claims does not indicate that a combination of these measures cannot be used to advantage.

The invention claimed is:

1. A photo acoustic detector for detecting a concentration of a sample in a sample mixture, the photo acoustic detector comprising:

a light source for producing a light beam for exciting molecules of the sample, a light modulator for modulating the light beam for generating pressure variations in the sample mixture, an amplitude of the pressure variations being a measure of the concentration, a detector element for converting the pressure variations into a detector current, and a processing section for processing the detector current to generate an output signal representing the concentration, wherein the processing section comprises:

an integrating amplifier for integrating the detector current, the integrating amplifier being coupled to the detector element via a hold switch, and a timing circuit for generating a hold signal, SWHOLD, for operating the hold switch in order to couple the integrating amplifier to the detector element during a predetermined interval of a period of the detector current, wherein the predetermined interval is shorter than the period of the detector current.

2. A photo acoustic detector for detecting a concentration of a sample in a sample mixture, the photo acoustic detector comprising:

a light source for producing a light beam for exciting molecules of the sample, a light modulator for modulating the light beam for generating pressure variations in the sample mixture, an amplitude of the pressure variations being a measure of the concentration, a detector element for converting the pressure variations into a detector current, and a processing section for processing the detector current to generate an output signal representing the concentration, wherein the processing section comprises:

an integrating amplifier for integrating the detector current, the integrating amplifier being coupled to the detector element via a hold switch, and a timing circuit for generating a hold signal, SWHOLD, for operating the hold switch in order to couple the integrating amplifier to the detector element during a predetermined interval of a period of the detector current, wherein the timing circuit is configured for operating the hold switch repeatedly by generating the hold signal, SWHOLD, as a periodic signal with a frequency equal to a frequency of the detector current and a duty cycle of 50%.

3. The photo acoustic detector according to claim 1, wherein the detector element comprises an oscillator element, and wherein the light modulator is configured for modulating the light beam at a resonance frequency of the oscillator element.

4. The photo acoustic detector according to claim 3, wherein the oscillator element comprises a crystal oscillator.

5. A photo acoustic detector for detecting a concentration of a sample in a sample mixture, the photo acoustic detector comprising:

a light source for producing a light beam for exciting molecules of the sample, a light modulator for modulating the light beam for generating pressure variations in the sample mixture, an amplitude of the pressure variations being a measure of the concentration, a detector element for converting the pressure variations into a detector current, and a processing section for processing the detector current to generate an output signal representing the concentration, wherein the processing section comprises:

an integrating amplifier for integrating the detector current, the integrating amplifier being coupled to the detector element via a hold switch, and a timing circuit for generating a hold signal, SWHOLD, for operating the hold switch in order to couple the integrating amplifier to the detector element during a predetermined interval of a period of the detector current, wherein the timing circuit is configured for operating the hold switch repeatedly by generating the hold signal, SWHOLD, as a periodic signal with a frequency equal to one third of the frequency of the detector current and a duty cycle of 50%.

6. A photo acoustic detector for detecting a concentration of a sample in a sample mixture, the photo acoustic detector comprising:

a light source for producing a light beam for exciting molecules of the sample, a light modulator for modulating the light beam for generating pressure variations in the sample mixture, an amplitude of the pressure variations being a measure of the concentration, a detector element for converting the pressure variations into a detector current, and a processing section for processing the detector current to generate an output signal representing the concentration, wherein the processing section comprises:

an integrating amplifier for integrating the detector current, the integrating amplifier being coupled to the detector element via a hold switch, and a timing circuit for generating a hold signal, SWHOLD, for operating the hold switch in order to couple the integrating amplifier to the detector element during a predetermined interval of a period of the detector current, wherein the timing circuit is configured for operating the hold switch repeatedly by generating the hold signal, SWHOLD, as a periodic signal with a frequency equal to half of the frequency of the detector current and a duty cycle of 75%.

7. The photo acoustic detector according to claim 2, wherein the processing section is configured for:

taking a first measurement and a second measurement by respectively generating a first output signal and a second output signal, the hold signal, SWHOLD, used for the second measurement being phase shifted over half a period of the detector current, and calculating an average output signal from absolute values of the first output signal and the second output signal.

8. The photo acoustic detector according to claim 1, wherein the hold switch is coupled to the detector element via a buffer stage.

9. A photo acoustic detector for detecting a concentration of a sample in a sample mixture, the photo acoustic detector comprising:

a light source for producing a light beam for exciting molecules of the sample, a light modulator for modulating the light beam for generating pressure variations in the sample mixture, an amplitude of the pressure variations being a measure of the concentration, a detector element for converting the pressure variations into a detector current, and a processing section for processing the detector current to generate an output signal representing the concentration, wherein the processing section comprises:

an integrating amplifier for integrating the detector current, the integrating amplifier being coupled to the detector element via a hold switch, and a timing circuit for generating a hold signal, SWHOLD, for operating the hold switch in order to couple the integrating amplifier to the detector element during a predetermined interval of a period of the detector current, wherein the processing section further comprises a select switch for copying an integrated voltage from the integrating amplifier to the output signal and a reset switch for resetting the integrating amplifier, wherein the timing circuit is configured for generating a select signal, SWSELECT, for operating the select switch and a reset signal, SWRESET, for successively operating the reset switch, and wherein the timing circuit is further configured for generating the hold signal, SWHOLD, with a frequency of at least twice a frequency of the reset signal, SWRESET.

10. A photo acoustic detector for detecting a concentration of a sample in a sample mixture, the photo acoustic detector comprising:

a light source for producing a light beam for exciting molecules of the sample, a light modulator for modulating the light beam for generating pressure variations in the sample mixture, an amplitude of the pressure variations being a measure of the concentration, a detector element for converting the pressure variations into a detector current, and a processing section for processing the detector current to generate an output signal representing the concentration, wherein the processing section comprises:

an integrating amplifier for integrating the detector current, the integrating amplifier being coupled to the detector element via a hold switch, and a timing circuit for generating a hold signal, SWHOLD, for operating the hold switch in order to couple the integrating amplifier to the detector element during a predetermined interval of a period of the detector current, wherein the processing section further comprises a post processing unit including:

a comparator for comparing an integrated voltage from the integrating amplifier to a predetermined value, a reset pulse generator for, when the integrated voltage reaches the predetermined value, providing a reset pulse, SWRESET, for closing a reset switch and resetting the integrating amplifier, and a timer for, when the integrated voltage reaches the predetermined value, determining a total sampling time used for reaching the predetermined value.

11. The photo acoustic detector of claim 3, wherein the oscillator element comprises a quartz tuning fork.

* * * * *